(12) United States Patent
Meythaler et al.

(10) Patent No.: US 9,655,968 B2
(45) Date of Patent: May 23, 2017

(54) BACLOFEN SOLUTION FOR LOW-VOLUME THERAPEUTIC DELIVERY

(71) Applicant: Wayne State University, Detroit, MI (US)

(72) Inventors: Jay M. Meythaler, Grosse Pointe Farms, MI (US); Stephen M. Tuel, Silver Spring, MD (US)

(73) Assignee: Wayne State University, Detroit, MI (US)

( * ) Notice: Subject to any disclaimer, the term of this patent is extended or adjusted under 35 U.S.C. 154(b) by 136 days.

(21) Appl. No.: 14/155,981

(22) Filed: Jan. 15, 2014

(65) Prior Publication Data

US 2014/0128355 A1 May 8, 2014

Related U.S. Application Data

(63) Continuation of application No. 12/664,503, filed as application No. PCT/US2008/066831 on Jun. 13, 2008.

(60) Provisional application No. 60/943,729, filed on Jun. 13, 2007.

(51) Int. Cl.
| | |
|---|---|
| *A61K 31/197* | (2006.01) |
| *A61K 45/06* | (2006.01) |
| *A61K 9/00* | (2006.01) |
| *A61K 31/195* | (2006.01) |
| *A61K 47/02* | (2006.01) |
| *A61K 31/192* | (2006.01) |

(52) U.S. Cl.
CPC ............ *A61K 45/06* (2013.01); *A61K 9/0019* (2013.01); *A61K 31/192* (2013.01); *A61K 31/195* (2013.01); *A61K 47/02* (2013.01)

(58) Field of Classification Search
None
See application file for complete search history.

(56) References Cited

U.S. PATENT DOCUMENTS

| | | | |
|---|---|---|---|
| 4,313,945 A | 2/1982 | Wiederkehr et al. | |
| 4,443,440 A | 4/1984 | Anderson et al. | |
| 4,467,101 A | 8/1984 | Kocsis et al. | |
| 4,493,832 A | 1/1985 | Teraji et al. | |
| 4,515,960 A | 5/1985 | Teetz | |
| 4,539,161 A | 9/1985 | Guglielmetti | |
| 4,727,160 A | 2/1988 | Teetz et al. | |
| 4,735,937 A | 4/1988 | Heusler et al. | |
| 4,855,290 A | 8/1989 | Fisher et al. | |
| 4,971,962 A | 11/1990 | Oh et al. | |
| 5,061,722 A | 10/1991 | Teetz et al. | |
| 5,073,539 A | 12/1991 | Mazzenga et al. | |
| 5,106,627 A | 4/1992 | Aebischer et al. | |
| 5,149,713 A | 9/1992 | Bousquet | |
| 5,583,218 A | 12/1996 | Takemura et al. | |
| 5,935,795 A | 8/1999 | Lin et al. | |
| 5,942,508 A | 8/1999 | Sawa | |
| 5,994,365 A | 11/1999 | Zaworotko et al. | |
| 6,028,223 A | 2/2000 | Ruminski et al. | |
| 6,252,075 B1 | 6/2001 | Shiragami et al. | |
| 6,500,809 B1 * | 12/2002 | Frazer .................... | A61K 31/19 424/570 |
| 6,548,555 B1 | 4/2003 | Curatolo et al. | |
| 6,656,172 B1 | 12/2003 | Hildebrand | |
| 6,831,199 B1 | 12/2004 | Ruminski et al. | |
| 6,969,383 B2 | 11/2005 | Hildebrand | |
| 7,175,856 B2 | 2/2007 | Ullah et al. | |
| 7,199,247 B2 | 4/2007 | Lemmens et al. | |
| 2006/0009523 A1 * | 1/2006 | Trissel ................. | A61K 31/195 514/561 |
| 2009/0123451 A1 * | 5/2009 | Dodge .................... | A61K 31/00 424/94.61 |
| 2010/0210604 A1 | 8/2010 | Meythaler | |

FOREIGN PATENT DOCUMENTS

WO    WO-2008157308    12/2008

OTHER PUBLICATIONS

Won et al., Brain Research 1123: 237-244, 2006.*
Samson-Fang, L. et al., Intrathecal baclofen withdrawal simulating neuroleptic malignant syndrome in a child with cerebral palsy, *Developmental Medicine & Child Neurology*, 42(8): 561-65, 2000.
Goda, R. et al., Simple and sensitive liquid chromatography tandem mass spectrometry method for determination of the S(+)- and R(?)-enantiomers of baclofen in human plasma and cerebrospinal fluid, *Journal of Chromatography B*, 801(2): 257-64, Mar. 5, 2004.
Allen et al., Stability of baclofen, captopril, diltiazem hydrochloride, dipyridamole, and flecainide acetate in extemporaneously compounded oral liquid, *Am J Health-Syst Pharm*, 53:2179-2184, 1996.
Fishman, R., Cerebrospinal Fluid in Disease of the Nervous System, Philadelphia Saunders 1980.
Berning, S. et al., Novel Treatment of Meningitis Caused by Multidrug-Resistant *Mycobacterium tuberculosis* with Intrathecal Levofloxacin and Amikacin: Case Report, *Brief Reports CID*, 32: 643-46, Feb. 2001.
Griffith, Endoneurosurgery: Endoscopic Intracranial Surgery, *Proceedings of the Royal Society of London, Series B, Biological Sciences*, 195(1119): 261-68, Jan. 14, 1977.
Griffith et al, The treatment of childhood hydrocephalus by choroid plexus coagulation and artificial cerebrospinal fluid perfusion, *British Journal of Neurosurgery*, 4: 95-100, 1990.

(Continued)

Primary Examiner — Svetlana M Ivanova
(74) Attorney, Agent, or Firm — Dinsmore & Shohl LLP

(57) ABSTRACT

A high concentration baclofen solution is provided suitable for therapeutic use in a medical setting. A high concentration solution of baclofen in multivalent physiological ion solution such as artificial cerebrospinal fluid is provided with concentrations of baclofen of 10 mg/ml. Artificial cerebrospinal fluid is particularly advantageous as a baclofen solvent. A medical package is also provided for baclofen delivery to patients suffering from spasticity.

9 Claims, No Drawings

(56) References Cited

OTHER PUBLICATIONS

Gupta et al, Quantitation of 4-(4-chlorophenyl)-2-pyrrolidine in baclofen powder and tablets, Drug Develop Indust Pharm, 14(11): 1623-28, 1998.
Jackson et al, a γ-aminobutyric acid$_B$ agonist reverses the negative feedback effect of testosterone on gonadotropin-releasing hormone and luteinizing hormone secretion in the male sheep, Endocrinology, 141(11): 3940-45, 2000.
Johnson et al, Stability of an extemporaneously compounded baclofen oral liquid, *Am J Hosp Pharm*, 50: 2353-55, 1993.
Lagarce et al, Baclofen-loaded microspheres in gel suspensions for intrathecal drug delivery: in vitro and in vivo evaluation, Eur J Pharm Biopharm, 61: 171-80, 2005.
Oka et al, The significance of artificial cerebrospinal fluid as perfusate and endoneurosurgery, Neurosugery, 38: 733-736, 1996.
Ross et al, Aqueous solubilities of some variously substituted quinolone antimicrobials, Intl. J. Pharm., 63: 237-250, 1990.
Schmuck, G. et al., Determination of the Excitatory Potencies of Fluoroquinolones in the Central Nervous System by an In Vitro Model, Antimicrobial Agents and Chemotherapy, 42(7): 1831-36, Jul. 1998.
Sitaram et al, Stability and compatibility of baclofen and morphine admixtures for use in an implantable infusion pump, Int J Pharm, 13-24:153, 1997.
Walwaikar, P. et al., Ofloxacin in multidrug resistant tuberculosis, J Indian Med Assoc., 101(3): 210-2, Mar. 2003 (Abstract).
Winslow et al, New transfusion strategies: red cell substitutes, Annual Review of Medicine, 50: 337-353, 1999.
Won, S. et al., Influence of age on the response to fibroblast growth factor-2 treatment in a rate model of stroke, Brain Research, 1123: 237-44, Oct. 24, 2006.

* cited by examiner

BACLOFEN SOLUTION FOR LOW-VOLUME THERAPEUTIC DELIVERY

REFERENCE TO RELATED APPLICATIONS

This application is a continuation of U.S. patent application Ser. No. 12/664,503, filed Dec. 14, 2009, which is a 371 application of PCT/US2008/066831, filed Jun. 13, 2008, which claims priority from U.S. Provisional Application Ser. No. 60/943,729, filed Jun. 13, 2007, the entire content of all of which is incorporated herein by reference.

FIELD OF THE INVENTION

This invention relates to the field of high concentration baclofen solutions in cerebrospinal fluid compatible solution suitable for clinical and research intrathecal administration and in particular to an artificial cerebrospinal fluid solution and medical package suitable for clinical delivery to patients and use in medical devices designed to deliver solution based baclofen to patients.

BACKGROUND OF THE INVENTION

Baclofen is a muscle relaxant and anti-spastic. Baclofen is useful for the alleviation of signs and symptoms of spasticity resulting from multiple sclerosis, particularly for the relief of flexor spasms and concomitant pain, clonus, and muscular rigidity. Baclofen is an analog of the putative inhibitory neurotransmitter gamma-aminobutyric acid (GABA). In studies with animals, baclofen has been shown to have general CNS depressant properties as indicated by the production of sedation with tolerance, somnolence, ataxia, and respiratory and cardiovascular depression. Baclofen is rapidly and extensively absorbed and eliminated. Absorption may be dose dependent, being reduced with increasing doses. Baclofen is excreted primarily by the kidney in unchanged form and there is relatively large intersubject variation in absorption and/or elimination.

The precise mechanism of action of baclofen as a muscle relaxant and anti-spasticity agent is not fully understood. Baclofen inhibits both monosynaptic and polysynaptic reflexes at the spinal level, possibly by decreasing excitatory neurotransmitter release from primary afferent terminals, although actions at supraspinal sites may also occur and contribute to its clinical effect. Baclofen is a structural analog of the inhibitory neurotransmitter GABA, and may exert its effects by stimulation of the $GABA_B$ receptor subtype. Bowery N G, et al., *Nature,* 1980; 283:92-94; Bowery N G, et al., *Neuroscience,* 1987; 20:365-383; Bowery, N G, et al., *Pharmacology Reviews,* 2002; 54:247-264; Meythaler J M. Use of intrathecally delivered medications for spasticity and dystonia in acquired brain injury. Yaksh, editor. *Spinal Drug Delivery.* Elsevier, N.Y. 1999, pp. 513-554; LIORESAL® INTRATHECAL (baclofen injection) product insert.

Baclofen is a white to off-white, odorless or practically odorless crystalline powder, with a molecular weight of 213.66 g/mol. It is slightly soluble in water, very slightly soluble in methanol, and insoluble in chloroform. LIORESAL® INTRATHECAL (baclofen injection) product insert.

Baclofen is currently the most effective treatment for severe spasticity and spastic hypertonia. This debilitating complication illustratively results from spinal cord injuries, multiple sclerosis, stroke, traumatic brain injuries, cerebral palsy and neurodegenerative diseases. Avellino A M, et al., *Neuromodulation,* 2000; 3:75-81. Spasticity is a debilitating complication that commonly leads to functional impairment, pain, and decreased personal independence. Id.

Oral baclofen therapy is approved. However, the oral therapy is commonly insufficient to reduce spasticity, and many patients are unresponsive. The high circulating concentrations of oral baclofen required for clinical efficacy produce numerous side effects including drowsiness, dizziness, weakness, ataxia, and confusion.

Administration of baclofen to patients with spinal or distal spasmodic conditions has proven to be a therapeutic challenge. Oral administration of baclofen is limited in that the maximum concentration of neural fluid baclofen is commonly insufficient to alleviate the spastic result of underlying etiology. Commonly, patients are unresponsive to oral baclofen administration or suffer intolerable side effects such as drowsiness, dizziness, weakness, ataxia, and confusion when efficacious levels of baclofen are present. Avellino, A M and Loeser, J D, *Neuromodulation,* 2000; 3:75-81.

In response to the non-optimal response to oral baclofen, programmable pump systems were developed that are implantable and provide a continuous infusion of baclofen directly to the cerebrospinal fluid. This method of delivery produces a more potent anti-spastic effect with fewer and less severe side effects. The pump is implanted subcutaneously whereby baclofen is transferred though a catheter to the lumbar region where it is passed through a Tuhoy needle directly into the cerebrospinal fluid. Albrigt, A L, et al., *Neurosurgery,* 2005; 56:93-97.

Intrathecal delivery of baclofen is more efficacious than oral delivery. However, it is not without complications. The most common complications include pump failure, infection, or migration of the catheter. Stempien, L, and Tsai, T, *Am J Phys Med Rehabil,* 2000; 79:536-41. However, cerebrospinal fluid (CSF) leaks are common with intrathecal delivery, particularly in children with cerebral palsy where an incidence rate of 6-15% is observed. Similar complications are also observed in adults at a rate of about 1%. Albrigt, A L, et al., *Neurosurgery,* 2005; 56:93-97. A possible explanation for CSF leakage is increased fluid pressure from the additional infusion volume from the pump or from occult hydrocephalus.

Baclofen is delivered intrathecally in saline that is loaded into the infusion pump by injection into a reservoir. The presence of the saline itself leads to toxicity and other complications. Injection of baclofen/saline solutions suffer neurotoxic complications resulting from their differing pH, osmotic pressure, membrane-active ion concentration, and $CO_2$. Oka, K, et al., *Neurosurgery,* 1996; 38:733-736; Griffith H B, *Endoneurosurgery: Endoscopic intracranial surgery,* in Symon L (ed): Advances and Technical Standards in Neurosurgery. Wien, Springer-Verlag, 1986; 4:2-24; Griffith, H B, and Jamjoom A B, *Br J Neurosurg,* 1990; 4:95-100.

The use of directed intrathecal or intraventricular administration of baclofen either by bolus injection or by continuous or non-continuous infusion regulated by refillable, implantable pump systems has drastically improved the clinical feasibility of baclofen administration. However, baclofen has poor solubility in aqueous solutions necessitating high volumes of infused baclofen solution to achieve efficacious doses. Further, the 2 mg/mL maximum saline concentration has been inadequate to control the spasticity, hypertonia and symptoms of some patients. An additional difficulty is that mixing a 2 mg/mL baclofen injection with other drugs such as morphine or hydromorphone in "cocktails" to aid in control of pain can dilute the baclofen content to unacceptably low levels.

Baclofen is supplied as a solid powder form or tablet. Most commonly baclofen is provided in a solution of baclofen, sodium chloride, and water. These solutions generally do not require preservatives or other stabilizers as dissolved baclofen has been calculated to degrade less than 10% over a 10-year period when maintained at near neutral pH and room temperature. Ahuja, *Analytical Profiles of Drug Substances*, 1985; Vol. 14, New York: Academic Press, pp. 527-548.

The practical solubility of baclofen in aqueous solutions has been extensively investigated. The upper limit of aqueous solubility has been estimated to be 4.3 mg/ml. (Ahuja, 1985.) This was only achieved following long term dissolution of powder baclofen requiring weeks or months and merely represents an equilibrium suspension not suitable for intrathecal delivery. Increased solubility has been achieved in aqueous saline solution to as high as 12 mg/ml following extreme heating to as much as 100° C. and intense agitation such as by sonication, or high speed stirring. U.S. Patent Application Publication 2006/0009523. The drawbacks of this method are that creating baclofen solutions is time consuming and requires instrumentation not commonly found in a clinical setting. Another method that has shown some success is by initial dissolution in acid solution with pH levels below 3.87. Just prior to administration a base is added to bring the pH to pharmaceutically acceptable levels. This back titration method produces baclofen concentrations of nearly 10 mg/ml. U.S. Patent Application Publication 2006/0009523. However, strong acids or bases are required for the initial baclofen solvation that persist as a component of the clinically delivered baclofen solution. Unfortunately, saline solutions suffer neurotoxic complications resulting from their differing pH, osmotic pressure, membrane-active ion concentration, and $CO_2$ making them unsuitable for intrathecal delivery directly into the CSF. Oka, K, et al., *Neurosurgery*, 1996; 38:733-736; Griffith H B: *Endoneurosurgery: Endoscopic intracranial surgery*, in Symon L (ed): Advances and Technical Standards in Neurosurgery. Wien, Springer-Verlag, 1986; 4:2-24; Griffith, H B, and Jamjoom A B, *Br J Neurosurg*, 1990; 4:95-100.

An alternative to saline or other aqueous solution for baclofen administration is artificial cerebrospinal fluid (aCSF). Differing forms of aCSF were previously used for in vivo pharmacological studies of baclofen administration. Jackson, G L, et al., *Endocrinology*, 2000; 141: 3940-3945; Goda, R. et al., *J Chromatogr B Analyt Technol Biomed Life Sci*, 2004; 801:257-64. However, the baclofen concentrations achieved in these and other studies were less than 0.21 mg/ml.

Thus, there exists a need for an improved solution in both concentration, stability, and compatibility with the CSF of baclofen for intrathecal delivery for the treatment of spasticity.

SUMMARY OF THE INVENTION

A solution of baclofen is provided wherein baclofen is solubilized in a multivalent physiological ion solution such as artificial cerebrospinal fluid at a concentration at or above 2 mg/ml and to 10 mg/ml. The pH of the inventive baclofen solution is between 5 and 8. The high concentration baclofen solution is suitable for delivery to a patient by a route including intrathecal, intraventrical, oral, intravenous, intra-arterial, intraperitoneal, epidural, intramuscular, or subcutaneous routes of delivery.

The high concentration baclofen solution is suitable for treating a disease or injury. Common diseases or injuries that are treatable by the inventive solution are spasticity, brain injury, cerebral palsy, spinal cord injury, cervical injury, multiple sclerosis, thoracic injuries, and spinal pathology.

Further provided is a medical package including a single or multidose ampule or ampules of inventive high concentration baclofen solution along with instructions for the treatment of an injury or disease such as spasticity.

The inventive high concentration baclofen solution is provided in a solvent containing 130-160 mM NaCl, 2.7-3.9 mM KCl, 1-10 mM $CaCl_2.2H_2O$, 0.5-10 mM $MgCl_2.6H_2O$ and a remainder water. Preferred concentrations of ingredients are 148 mM NaCl; 3 mM KCl; 1.4 mM $CaCl_2.2H_2O$; 0.8 mM $MgCl_2.6H_2O$; 0.8 mM $Na_2HPO_4.7H_2O$; 0.2 mM $NaH_2PO_4.H_2O$. The solution optionally also contains 0.5-1.0 mM $Na_2HPO_4$ and 0.1-0.5 mM $NaH_2PO_4$ and/or 15-35 mM $HCO_3$. The pH of the inventive solutions is at or between 5 and 8.

The inventive high concentration baclofen solution is suitable to be used in combination with other therapeutics such as one or more pain regulating agents that illustratively include morphine, clonidine, hydromorphine, hydrocodone, merperidine, celeroxib, tramadol, oxycodone, acetominophen, ketaprofen, ibuprofen, naproxen sodium, aspirin, and combinations thereof.

DETAILED DESCRIPTION OF THE PREFERRED EMBODIMENTS

The present invention has utility as a therapeutic or research baclofen solution for control of spastic or other complications of underlying disease or injury. The present invention allows for high concentrations of baclofen to be administered to patients so as to increase the likelihood of clinical benefit and allowing for simultaneous administration of other clinical compounds such as pain modulators. It will also allow for improved compatibility within the CSF.

A process is herein provided for increasing the solubility of baclofen without resort to the procedure of U.S. Patent Application Publication 2006/0009533 and in a solution more biologically similar to the physiological environment of cerebrospinal fluid. Moreover, the inventive procedure achieves high baclofen concentrations in the without dependence on strong acids or strong bases for initial solvation. As it was known in the art that baclofen is modestly soluble in water or saline to a concentration below 2 mg/mL, and studies indicated that low solubility had been achieved in forms of artificial cerebrospinal fluid, solid baclofen was dissolved in multivalent physiologic ion solutions (MPI), and preferably aCSF at increasing final concentrations. Surprisingly, MPI solution did not behave similar to other aqueous solvent solutions when acting as a solvent for baclofen. Baclofen rapidly dissolves in MPI solution at 0.1 to 2 mg/ml final concentration. More surprisingly, the solubility of baclofen in MPI solution extended beyond the expected level of 2 mg/ml, and solubility of 6 mg/ml was rapidly achieved without the need for sonication or excessive agitation as was required to achieve the prior art saline solutions.

As used herein, the term multivalent physiological ion solution (MPI) means any aqueous or non-aqueous liquid solution containing at least one divalent cation of magnesium or calcium, and at least one anion of carbonate or phosphate of a pH between 6 and 8.5. It is appreciated that other physiological ions such as sodium, potassium, onium and chloride are optionally provided. Preferably, the MPI solution is within 30% of isotonicity relative to cerebrospinal fluid. MPI solution also optionally includes an additive, illustratively, glucose, oncotic agents, plasma extenders, and oxygen carrying components. Optionally, the inventive MPI baclofen solution is saturated with 95% oxygen and 5% carbon dioxide.

As used herein the term artificial cerebrospinal fluid (aCSF) means any multivalent physiological ion solution designed to mimic physiological cerebrospinal fluid. aCSF is illustratively a MPI solution. aCSF illustratively contains 130-160 mM NaCl; 2.7-3.9 mM KCl; 1-10 mM $CaCl_2.2H_2O$; 0.5-10 mM $MgCl_2.6H_2O$; 0.5-5 mM $Na_2HPO_4.7H_2O$; 0.1-2 mM $NaH_2PO_4.H_2O$. Preferably, aCSF is comprised of 148 mM NaCl; 3 mM KCl; 1.4 mM $CaCl_2.2H_2O$; 0.8 mM $MgCl_2.6H_2O$; 0.8 mM $Na_2HPO_4.7H_2O$; 0.2 mM $NaH_2PO_4.H_2O$. Additional or alternative components of aCSF are illustratively 20-25 mM sodium carbonate, 0.5-1.5 mM glucose, 200-450 mg/ml oncotic agent, or 5-20% oxygen carrying component. The pH of aCSF is optionally at or between 3 and 10.

As used herein the term delivery means any administration of baclofen to a mammal, other animal, or as used in in vitro research.

As used herein the term patient means any animal. Illustratively, the term patient means a mammal. Preferably, a mammal illustratively includes humans, mice, rats, guinea pigs, rabbits, dogs, cats, swine, bovine, monkey, baboon, chimpanzees.

As used herein the term disease or injury means any physiologically abnormal state. Illustrative examples of a disease or injury are spasticity, brain injury, cerebral palsy, spinal cord injury, cervical injury, multiple sclerosis, thoracic injuries, and spinal pathology, or combinations thereof.

As used herein the term dose means any amount of active therapeutic ingredient, such as baclofen or a pain regulating agent delivered to a mammal, other animal, or as used in in vitro research.

As used herein the term pain regulating agent is any agent that serves to decrease, increase, or otherwise modulate pain. Non-limiting examples include morphine, clonidine, hydromorphine, hydrocodone, merperidine, celeroxib, tramadol, oxycodone, acetominophen, ketaprofen, ibuprofen, naproxen sodium, and aspirin. It is appreciated in the art that other chemical compounds are similarly operable to modulate pain.

A MPI solution of the present invention includes at least one divalent cation of magnesium or calcium, and at least one anion of carbonate or phosphate of a pH between 6 and 8.5. Other physiological ions such as sodium, potassium, onium and chloride are optionally provided. Preferably, the MPI solution is within 30% of isotonicity relative to cerebrospinal fluid. An MPI solution also optionally includes an additive, illustratively, glucose, oncotic agents, plasma extenders, and oxygen carrying components. The identity of such additives is further detailed below. Optionally, the inventive MPI baclofen solution is saturated with 95% oxygen and 5% carbon dioxide to mimic inventive physiologic gas concentration. Most preferably, an inventive MPI solution is based on artificial cerebrospinal fluid.

Artificial cerebrospinal fluid is composed generally of physiological ions in a carbonate or phosphate buffered solution. This solution illustratively contains 130-160 mM NaCl; 2.7-3.9 mM KCl; 1-10 mM $CaCl_2.2H_2O$; 0.5-10 mM $MgCl_2.6H_2O$; 0.5-5 mM $Na_2HPO_4.7H_2O$; 0.1-2 mM $NaH_2PO_4.H_2O$. Preferably, aCSF is comprised of 148 mM NaCl; 3 mM KCl; 1.4 mM $CaCl_2.2H_2O$; 0.8 mM $MgCl_2.6H_2O$; 0.8 mM $Na_2HPO_4.7H_2O$; 0.2 mM $NaH_2PO_4.H_2O$. Additional or alternative components of aCSF are illustratively 20-25 mM sodium carbonate, 0.5-1.5 mM glucose, 200-450 mg/ml oncotic agent, or 5-20% oxygen carrying component. U.S. Pat. No. 6,500,809. Oncotic agents are illustratively proteins naturally found in plasma (e.g. the albumin, globulin, and fibrinogen fractions), mixtures of such proteins derived from human blood plasma (commonly called plasma protein fraction), plasma extenders such as the dextrans (glucose polymers of preferably 40,000 to about 80,000 average molecular weight) and starch 2-hydroxyethyl ether (sold as Hespan by DuPont), dextrins (cyclodextrin), carboxymethyl cellulose, polyethylene glycol, glycogen, and pluronic acid. Oxygen carrying components suitable in the instant invention include perfluorocarbon-based products, cell-free hemoglobin, and liposome encapsulated hemoglobin among others. Winslow, R M, *Annual Review of Medicine,* 1999; 50:337-353. Each of the above reagents are available by clinical or research suppliers known in the art. The pH of the above solutions is preferably at or between 3 and 10. More preferably, the pH is at or between 5 and 8.

An inventive baclofen solution is provided that has higher baclofen concentration than is achievable in saline, or other aqueous solvents alone. In particular, baclofen concentrations are greater than 2 mg/ml in an MPI solution. Preferably, concentrations of baclofen are at or between 2 and 10 mg/ml inclusive in artificial cerebrospinal fluid. More preferably, baclofen concentrations are at or between 2 to 6.5 mg/ml in artificial cerebrospinal fluid.

The high baclofen solubility in an MPI solution was surprising given prior attempts to solubilize baclofen that produced limiting concentrations of only 0.2 mg/ml in aCSF. Jackson, G L, et al., *Endocrinology,* 2000; 141: 3940-3945; Goda, R. et al., *J Chromatogr B Analyt Technol Biomed Life Sci,* 2004; 801:257-64. Moreover, the long unmet medical need for an increased concentration of baclofen in a solution that does not itself produce unwanted side effects counseled against dissolving baclofen in aCSF to achieve high concentrations such as in the instant invention. Ahuja, *Analytical Profiles of Drug Substances,* 1985; Vol. 14, New York: Academic Press, pp. 527-548; Jackson, G L, et al., *Endocrinology,* 2000; 141: 3940-3945; Goda, R. et al., *J Chromatogr B Analyt Technol Biomed Life Sci,* 2004; 801:257-64. Indeed, the knowledge in the art taught away from the present invention in that baclofen was known to have an upper limit of solubility in aqueous solvents of only 2 mg/ml. Ahuja, *Analytical Profiles of Drug Substances,* 1985; Vol. 14, New York: Academic Press, pp. 527-548. Further, the labor, time, and cost intensive steps used by prior practitioners to increase baclofen solubility suggested that a simple solution, such as the instant invention, was untenable. U.S. Patent Application Publication 2006/0009523. Thus, the 2-6.5 mg/ml baclofen solution of the present invention was not considered in the art.

Baclofen suitable for use in the present invention is of any stable appropriate form for addition to an MPI solution. Preferably, baclofen is provided in tablet form such as supplied by Novartis under the name LIORESAL, or in powder form as a racemic mixture or as individual enantiomers from illustratively available from Sigma-Aldrich Corp., St. Louis, Mo. Presently, baclofen is commercially available for injection as a 2 mg/mL solution having a pH of 5 to 7 and the following simple preservative-free formula (LIORESAL INTRATHECAL package insert): Baclofen, 2 mg; Sodium chloride, 9 mg; Water for injection, qs 1 mL.

The compositions and processes of the invention are optionally used to treat mammalian subjects (e.g., sport or pet mammals such as dogs, cats, and horses, and humans).

Additionally, the inventive compositions and processes are optionally used for, but are not limited to research purposes such as in clinical or preclinical in vivo animal studies involving mammals illustratively including mice, rats, guinea pigs, rabbits, dogs, cats, swine, bovine, monkey, baboon, chimpanzee, and humans. It is further appreciated that the high concentration baclofen solutions are uniquely suited for in vitro research studies.

Baclofen is illustratively used in the treatment of intractable spasticity of the spine or brain etiology. Non-limiting examples of disease states or injuries suitable for treatment with the instant invention are spasticity, brain injury, cerebral palsy, spinal cord injury, cervical injury, multiple sclerosis, thoracic injuries, and spinal pathology.

The increased concentration of baclofen achieved in the instant invention allows for subsequent dilution by the addition of other components that are to be simultaneously infused with the baclofen. Spasticity is a painful complication, and patients often require pain regulating medications. Pain relieving medications suitable for combination with the inventive baclofen solution are illustratively morphine, clonidine, hydromorphine, hydrocodone, merperidine, celeroxib, tramadol, oxycodone, acetaminophen, ketaprofen, ibuprofen, naproxen sodium, and aspirin. It is appreciated in the art that other chemical compounds are similarly suitable for co-administration with baclofen in the instant invention.

The instant invention also provides a process of delivery of the highly concentrated baclofen solution. The inventive solution is illustratively delivered to the patient by intrathecal, intraventrical, oral, intravenous, intra-arterial, intraperitoneal, epidural, intramuscular, or subcutaneous delivery routes. There are numerous methods of injection known in the art illustratively including direct injection by the attending physician or other caregiver and the use of a continuous infusion pump system. An illustrative example of a pump system is that marketed under the trade name ACCU-CHECK by Disetronic, Fishers, Ind. The infusion pump is illustratively implantable, external, manual, or automatically regulated. Illustratively, the pump or manual infusion is by discontinuous administration.

In further embodiments, stable baclofen solutions of the present invention are provided in a medical package of baclofen solution illustratively suitable for injection, infusion, or other route of administration including oral. In a preferred embodiment the medical package contains a high concentration baclofen solution in MPI solution and an optional second source of MPI solution diluent that is optionally used to adjust the dosing volume or concentration. The baclofen solution is preferably provided free of pyrogens, antioxidants, preservatives or other potentially neurotoxic additives. In a particular package, the baclofen solution and diluent are provided in single dose ampules, however, it is appreciated that a single ampule optionally contains partial or multiple dose volumes and concentrations. In a preferred embodiment the ampule is designed to operate in conjunction with an implantable pump and contains sufficient baclofen solution such that continuous infusion may be maintained for 3 months or longer. Alternatively, the medical package is suitable for oral administration in liquid, tablet, powder, capsule, suspension, or other delivery form recognized in the art. In an alternative embodiment the baclofen solution is provided in a preloaded syringe that is suitable for manual injection or association with a syringe pump or other apparatus for longer infusion or injection times. Implantable infusion pumps generally designed for intrathecal baclofen administration are commonly recharged by addition of additional therapeutic by injection into a reservoir in the pump. It is appreciated that the medical package of the instant invention is suitable for recharging both implantable and external pumps, as well as for direct delivery to the patient in the absence of a pump such as for initial test dosing of baclofen. Common medical packages for baclofen are described in U.S. Patent Application Publication 2006/0009523. Preferably, a medical package includes instructions for the use thereof to treat a disease or injury resulting in spasticity.

Various aspects of the present invention are illustrated by the following non-limiting examples. The examples are for illustrative purposes and are not a limitation on any practice of the present invention.

EXAMPLE 1

Multivalent physiologic ion solution formation. A solution (A) is produced with 8.66 g NaCl, 0.224 g KCl, 0.206 g $CaCl_2.2H_2O$ and 0.163 g $MgCl_2.6H_2O$ dissolving in 500 mL of deionized water. A solution (B) is produced with 0.214 g $Na_2HPO_4.7H_2O$ and 0.027 g $NaH_2PO_4.H_2O$ dissolving in 450 mL of water. The pH is adjusted to 6.0, 6.5, 7.0, 7.3, 7.6 and 8.0 as necessary with either NaOH or $H_3PO_4$ and dilution to final volume of 500 mL with deionized water. A final multivalent physiologic ion solution is obtained by mixing equal parts of Solution A and B. pH is tested and adjusted to the desired final pH if necessary. All reagents are available from sources known in the art. Illustratively, reagents are available from Sigma-Aldrich Corp., St. Louis, Mo.

EXAMPLE 2

Baclofen solubilization study in multivalent physiologic ion solution. Baclofen raw material is weighed and 200.0±3.0 mg is added into each of six scintillation vials. To each vial is added 20.0 mL of the pH adjusted MPI of Example 1 (6.0, 6.5, 7.0, 7.3, 7.6 and 8.0). Solutions are warmed to 37° C. in a water bath. Each solution is manually mixed every minute during the first five minutes and at five minute intervals thereafter for the entire 30 minute aliquot pull period. Visually clear solutions are immediately obtained, but gentle stirring or vortexing is applied to the samples for several seconds to ensure complete solubilization of the baclofen. Clear solutions present with no visual particulate matter remaining. Approximately 5 mL aliquots are pulled at 2, 5 and 30 minutes of incubation using a syringe equipped with a 10 micron filter tip. The aliquots are analyzed by high performance liquid chromatography (HPLC). For analyses, 2.0 mL of each aliquot is transferred to a 20 mL volumetric flask containing mobile phase to produce a maximum sample concentration of 1.0 mg/mL. Additional linearity standards are optionally added. Baclofen concentrations above 4 mg/ml are readily achieved.

EXAMPLE 3

Baclofen solubilization in artificial cerebrospinal fluid. Baclofen powder is titrated with pH 7.3 MPI per Example 2 that is warmed to 37° C. A light box is used to identify the presence of precipitate. The volume added to the nearest 0.05 mLs. Aliquots of approximately 5 mL are removed with a syringe equipped with a 10 micron filter tip and analyzed by HPLC. Visually clear solutions are immediately obtained, but gentle stirring or vortexing is applied to the samples for several seconds to ensure complete solubilization of the baclofen. Baclofen concentrations are achieved in aCSF at 2, 2.5, 3, 3.5, 4, 4.5, 5, 5.5 and 6 mg/ml. Solutions with greater than 5 mg/ml final concentrations infrequently require gentle agitation for 2 minutes or less. Clear solutions are achieved with no visual particulate matter remaining.

EXAMPLE 4

Analyses of baclofen solutions to confirm concentrations. Baclofen concentrations of Examples 2 and 3 are determined to confirm soluble levels in MPI or aCSF in the inventive solutions. Baclofen concentrations are quantified by LC/MS/MS using an Applied Biosystems API 400 electrospray triple quadrupole mass spectrometer. Lagarce, F, et al., *Eur J Biopharm,* 2005, 61:171-80. Baclofen is separated on a $C_8$ 5 μm 100×2.1 mm column in which the mobile phase is composed of 60% $H_2O$/40% acetonitrile at a solvent flow of 250 μl/min following a 20 μl sample injection. The transition between 214.1 and 151.2 is used for quantification. All samples are confirmed with less than 5% variation from expected values.

EXAMPLE 5

Analyses of baclofen solutions to confirm concentrations. Alternatively, HPLC analyses of solutions prepared as in Example 2 or 3 are used to confirm baclofen concentrations in the visually clear solution as described in U.S. Patent Application Publication 2006/0009523; Sitaram B R, et al., *Int J Pharm,* 1997; 153:13-24; Gupta V D, and Parasrampuria J, *Drug Develop Indust Pharm,* 1998; 14:1623-1628; Johnson C E, et al., *Am J Hosp Pharm,* 1993; 50:2353-55; Allen L V, et al., *Am J Health-Syst Pharm,* 1996; 53:2179-2184. Solutions are filtered through a 0.22-micron filter to remove any particulate matter. Baclofen is separated on a $C_{18}$ 5 μm 250×4.6 mm column with a mobile phase gradient of 0.085 M ammonium phosphate (78.5%) and acetonitrile (21.5%) to acetonitrile (100%) as previously described. Id. Detection was by UV at 220 nm. In this system baclofen has a retention time of 4.7 min and decomposition products are present at 3.3, 6.4, and 17 min. Baclofen concentrations are determined within 10% of expected values.

TABLE 1

HPLC Analytical Method Used
Baclofen[a]

| Column: | Symmetry $C_{18}$ 5 μm, 250 × 4.6 mm i.d. |
|---|---|
| Mobile Phase: | A. 0.085M ammonium phosphate 78.5% and acetonitrile 21.5% |
| | B. Acetonitrile 100% |
| Flow Rate: | Gradient. See Table 2. |
| Detection: | UV 220 nm, 1.0 AUFS |
| RetentionTimes: | |
| Baclofen | 4.7 min |
| Decomposition products | 3.3, 6.4, 17 min |

[a]Precision: Mean ± S.D. (n = 10) 99.8 ± 1.0 μg/mL; percent relative standard deviation was 1.0%. Standard curves range was baclofen 50 to 150 μg/mL. Correlation coeffients were >0.9999.

TABLE 2

HPLC Mobile Phase Gradient Table

| Time (min) | Flow (mL/min) | A (%) | B (%) |
|---|---|---|---|
| 0 | 0.8 | 100 | 0 |
| 5 | 0.8 | 100 | 0 |
| 6 | 1.0 | 77 | 23 |
| 13 | 1.0 | 77 | 23 |
| 15 | 1.0 | 100 | 0 |
| 23 | 1.0 | 100 | 0 |
| 25 | 0.8 | 100 | 0 |

EXAMPLE 6

Administration of high concentration baclofen solution intrathecally. Patients presenting with spasticity who have undergone subcutaneous placement of a programmable intrathecal baclofen pump (Medtronic SyncroMed Infusion System; Medtronic, Inc, Minneapolis, Minn.) are administered baclofen at appropriate dosage levels by intrathecal delivery. The inventive baclofen solution is optionally supplemented with a pain regulating medication such as morphine at appropriate dosage levels and is simultaneously loaded into the infusion pump for intrathecal delivery. Patients are monitored in the hospital for two to four days while dose is increased to achieve measurable spasticity reduction without debilitating side effects. Additional follow up is at 1 month and every three months subsequently. Avellino A M, et al., *Neuromodulation,* 2000; 3:75-81.

Administration of baclofen solution to mammals. Baclofen solution of Example 2 or 3 is administered to adult rats essentially as described by Seong, J Y, et al., *Endocrinology,* 1995; 136:2587-93. Briefly, adult female rats of 250 g mean body weight and maintained under conditions of light on from 0700 h-1900 h, room temperature 23° C., water and food available ad libitum are ovarectomized and allowed to recover for two weeks. A stainless steel cannula is inserted as described. Following recovery of one week, rats are injected with baclofen at 1 mg/ml in aCSF. Animals are studied for therapeutic and pharmacological effects of Baclofen.

Alternatively, baclofen solution of Example 2 or 3 is administered to Wistar rat brain by superfusion essentially as described by Cesar, K, et al., *Proc. Nat. Acad. Sci, USA,* 2003; 100:16000-05. Briefly, a $0.4 \times 10^{-2}$ mg/ml solution of baclofen in aCSF is administered to anesthetized rats maintained to basic physiologic parameters of pH, $pO_2$, and $pCO_2$ by topical superfusion via an open cranial window prepared as described. Electrophysiological and other parameters are recorded prior to and following baclofen administration.

Administration of Baclofen to cats. Cats are administered baclofen essentially as described in U.S. Pat. No. 5,149,713. Cats weighing from 1.5 to 3.5 kg (n=4) are anaesthetized using pentobarbital (from 30 to 40 mg/kg administered first i.p., and then from 3 to 5 mg/kg administered i.v.) and then tracheotomised, curarised and ventilated artificially. The various basic haemodynamic parameters are recorded: arterial systolic and diastolic pressures, cardiac frequency, cardiac output. The various haemodynamic indices and parameters are also calculated (mean arterial pressure, dP/dt, double product frequencyxpressure).

The core temperature of the animals is maintained at from 37° to 37.5° C. by means of an electric blanket. The animals are placed in a stereotactic apparatus and then the defense area is stimulated electrically by means of an electrode placed in the grey matter, at coordinates $A_6L_1H_0$. The stimuli are supplied by a stimulator functioning in monopolar manner: frequency 100 Hz, duration 3 msec., difference in potential 3 to 6 volts.

The positioning of the electrode is considered to be satisfactory when the cardiac output and dP/dt are increased by more than 20%.

The baclofen is administered via the femoral vein. The animals are given 0.5 mg/kg or 1 mg/kg as the case may be. The various parameters are then recorded 15 minutes and 30 minutes after the injection of baclofen.

EXAMPLE 7

Clinical Study of Baclofen Administration in Humans.

Baclofen administration in humans in conjunction with Ziconotide is performed essentially as described in U.S. Pat. No. 7,268,109. The patient population includes male and female human patients on a dose of intrathecal baclofen (either compounded baclofen or LIORESAL®) ranging between 22 and 800 mg/day. Patient has pain and sub optimal pain relief indicated by a minimum VASPI of 40 mm at the Screening and Baseline Visit.

All patients must be on stable doses of LIORESAL® (between 22 and 800 µg/d), systemic opioids, and other concomitant medications for at least 7 days prior to the baseline visit. The contents of the SynchroMed® EL Infusion System are removed and replaced with PRIALT™ and LIORESAL®. The LIORESAL® dose remains the same as during the last 7 days of the screening period and throughout the first 9 weeks of the trial. The initial dose of PRIALT™ is 0.025 µg/hr (0.6 µg/d).

All patients must be on stable doses of LIORESAL® (between 22 and 800 µg/d), systemic opioids, and other concomitant medications for at least 7 days prior to the Baseline Visit. The contents of the SynchroMed® EL Infusion System are removed and replaced with PRIALT™ and LIORESAL®.

The LIORESAL® dose remains the same as during the last 7 days of the screening period and throughout the first 9 weeks of the trial. The initial dose of PRIALT™ is 0.025 µg/hr (0.6 µg/d). The pump flow rate is held constant and is at least 12 mcl/hr (288 mcl/d) to allow for clearance of the pump volume within one or two days. Drug dosage is not to be adjusted by changing the pump flow rate as this would change the rate of infusion of both compounds.

Spasticity scales (Modified Ashworth Scale: 0-4 normal to rigid tone; Spasm Scale 0-4 no spasms to greater than 10 per hr; Penn Spasm Frequency Scale, Visual Analogue of Spasticity Scale or VASS) is determined at each clinic visit.

Various modifications of the present invention, in addition to those shown and described herein, will be apparent to those skilled in the art of the above description. Such modifications are also intended to fall within the scope of the appended claims.

Patents and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The following references are each incorporated herein by reference as if the contents of each reference were fully and explicitly included.

REFERENCE LIST

1. Bowery N G, et al., *Nature,* 1980; 283:92-94
2. Bowery N G, et al., *Neuroscience,* 1987; 20:365-383
3. Bowery, N G, et al., *Pharmacology Reviews,* 2002; 54:247-264
4. Meythaler J M, Use of intrathecally delivered medications for spasticity and dystonia in acquired brain injury. Yaksh, editor. *Spinal Drug Delivery.* Elsevier, N.Y. 1999, pp. 513-554
5. LIORESAL® INTRATHECAL (baclofen injection) product insert
6. Avellino A M, et al., *Neuromodulation,* 2000; 3:75-81
7. Albrigt, A L, et al., *Neurosurgery,* 2005; 56:93-97
8. Stempien, L, and Tsai, T, *Am J Phys Med Rehabil,* 2000; 79:536-41
9. Oka, K, et al., *Neurosurgery,* 1996; 38:733-736
10. Griffith H B, *Endoneurosurgery: Endoscopic intracranial surgery,* in Symon L (ed): Advances and Technical Standards in Neurosurgery.
11. Wien, Springer-Verlag, 1986; 4:2-24
12. Griffith, H B, and Jamjoom A B, *Br J Neurosurg,* 1990; 4:95-100
13. Ahuja, *Analytical Profiles of Drug Substances,* 1985; Vol. 14, New York: Academic Press, pp. 527-548
14. U.S. Patent Application Publication 2006/0009523
15. Jackson, G L, et al., *Endocrinology,* 2000; 141: 3940-3945
16. Goda, R. et al., *J Chromatogr B Analyt Technol Biomed Life Sci,* 2004; 801:257-64
17. Mazzenga G C, Berner B. Transdermal delivery of zwitterionic drugs. Solubility of zwitterionic drugs. *Journal of Controlled Release,* 1991; 16:77-88
18. U.S. Pat. No. 6,500,809
19. Winslow, R M, *Annual Review of Medicine,* 1999; 50:337-353
20. Lagarce, F, et al., *Eur J Biopharm,* 2005, 61:171-80
21. Sitaram B R, et al., *Int J Pharm,* 1997; 153:13-24
22. Gupta V D, and Parasrampuria J, *Drug Develop Indust Pharm,* 1998; 14:1623-1628
23. Johnson C E, et al., *Am J Hosp Pharm,* 1993; 50:2353-55
24. Allen L V, et al., *Am J Health-Syst Pharm,* 1996; 53:2179-2184
25. Seong, J Y, et al., *Endocrinology,* 1995; 136:2587-93
26. Cesar, K, et al., *Proc. Nat. Acad. Sci, USA,* 2003; 100:16000-05
27. U.S. Pat. No. 5,149,713
28. U.S. Pat. No. 7,268,109

The invention claimed is:

1. A process for increasing the solubility of baclofen without use of strong acids or strong bases for initial solvation of the baclofen, and without sonication and without intense agitation to dissolve the baclofen, comprising dissolving baclofen in a multivalent physiological ion solution consisting essentially of 130-160 mM NaCl, 2.7-3.9 mM KCl, 1-10 mM $CaCl_2.2H_2O$, 0.5-10 mM $MgCl_2.6H_2O$ and a remainder water, wherein a concentration of dissolved baclofen of greater than 2 mg/ml and up to 10 mg/ml in the multivalent physiological ion solution is achieved, producing a baclofen solution for low-volume therapeutic delivery, wherein no visual particulate matter is present in the baclofen solution.

2. The process of claim 1 wherein the multivalent physiological ion solution further comprises 0.5-1.0 mM Na$_2$HPO$_4$ and 0.1-0.5 mM NaH$_2$PO$_4$.

3. The process of claim 1 wherein the multivalent physiological ion solution further comprises 148 mM NaCl; 3 mM KCl; 1.4 mM CaCl$_2$.2H$_2$O; 0.8 mM MgCl$_2$.6H$_2$O; 0.8 mM Na$_2$HPO$_4$.7H$_2$O; 0.2 mM NaH$_2$PO$_4$.H$_2$O.

4. The process of claim 1 wherein the pH of the multivalent physiological ion solution is at or between 5 and 8.

5. The process of claim 1 wherein the multivalent physiological ion solution further comprises 15-35 mM HCO$_3$.

6. The process of claim 1 wherein the baclofen solution further comprises one or more pain regulating agents selected from the group consisting of: morphine, clonidine, hydromorphine, hydrocodone, merperidine, celeroxib, tramadol, oxycodone, acetominophen, ketaprofen, ibuprofen, naproxen sodium, aspirin, and combinations thereof.

7. A method of treatment of a disease or injury selected from the group consisting of: spasticity, brain injury, cerebral palsy, spinal cord injury, cervical injury, multiple sclerosis, thoracic injuries, spinal pathology, and combinations thereof comprising delivery of the baclofen solution prepared by the process of claim 1 to a patient having the disease or injury.

8. The method of claim 7 wherein said delivery is selected from the group consisting of: intrathecal, intraventrical, oral, intravenous, intra-arterial, intraperitoneal, epidural, intramuscular, and subcutaneous delivery.

9. The method of claim 7 wherein the baclofen solution is administered by intrathecal delivery to a patient by manual or automatic injection apparatus.

* * * * *